United States Patent [19]

Nakajima et al.

[11] Patent Number: 4,689,136
[45] Date of Patent: Aug. 25, 1987

[54] OXYGEN SENSOR ASSEMBLY

[75] Inventors: Toyohei Nakajima, Shiki; Toshiyuki Mieno, Niiza, both of Japan

[73] Assignee: Honda Giken Kogyo Kabushiki Kaisha, Tokyo, Japan

[21] Appl. No.: 808,081

[22] Filed: Dec. 12, 1985

[30] Foreign Application Priority Data

Jan. 28, 1985 [JP] Japan ............. 60-010241[U]

[51] Int. Cl.⁴ ............................................ G01N 27/46
[52] U.S. Cl. ................................... 204/428; 204/425;
204/426
[58] Field of Search ............... 204/425, 426, 427, 428,
204/429, 15; 338/34; 123/489; 60/276

[56] References Cited

U.S. PATENT DOCUMENTS 4,184,934  1/1980  Bode et al. .................... 204/428
4,199,424  4/1980  Teitelbaum .................... 204/428
4,476,008 10/1984  Sano et al. .................... 204/425

*Primary Examiner*—T. Tung
*Attorney, Agent, or Firm*—Birch, Stewart, Kolasch & Birch

[57] ABSTRACT

An oxygen sensor comprising an oxygen sensing unit sensitive to oxygen in an oxygen-containing gas and operative to produce an electric signal variable with the concentration of oxygen in the oxygen-containing gas when contacted by a stream of the gas, and a partitioned housing structure which has at least one first port open to the outside of the housing structure and which comprises partition means defining in the housing structure first and second chambers which are located across the partition means, the partition means being formed with at least one second port providing communication between the first and second chambers, the first chamber being open to the first port and the second chamber having enclosed the oxygen sensing unit therein. When such an oxygen sensor assembly is incorporated into the exhaust system of an internal combustion engine in which the exhaust gases normally involves pulsation of the gas pressure, the pulsating gas pressure of the exhaust gases allowed into the receptacle through the port therein can be dampened out before the gases reach the oxygen sensing unit and enables the sensing unit to detect the concentration of oxygen in the gases at practically constant, relatively low pressure levels.

4 Claims, 12 Drawing Figures

PRIOR ART

PRIOR ART

FIG. 6

PRIOR ART

OXYGEN SENSOR ASSEMBLY

FIELD OF THE INVENTION

The present invention relates to a sensor for determining the concentration of oxygen in an oxygen-containing atmosphere in an enclosed volume and, more particularly, to an electrochemical oxygen sensor assembly adapted to determine the concentration of oxygen in, typically, exhaust gases from an automotive internal combustion engine.

BACKGROUND OF THE INVENTION

Various feedback control systems are known and used to clean exhaust gases from automotive internal combustion engines. Such a control system uses an electric signal generated by an oxygen sensor operative to detect and determine the concentration of oxygen in the exhaust gases from an internal combustion engine. The electric signal thus produced by the oxygen sensor is processed with a view to cleaning the exhaust gases from the engine and enables the control system to properly regulate the air-to-fuel ratio of the combustible mixture to be inducted into the combustion chambers of the engine.

Among the various types of oxygen sensors used for such exhaust-gas cleaning purposes, there is an electrochemical oxygen sensor using an oxygen-ion conductive solid electrolyte as an active material. An example of an electrochemical oxygen sensor of this type is disclosed in U.S. Pat. No. 4,450,065. The electrochemical oxygen sensor shown in this published Patent is operative to generate a voltage output which varies in proportion to the detected concentration of oxygen. A feedback control using this oxygen sensor is, for this reason, capable of regulating the air-to-fuel ratio with far more subtleness than could be achieved by means of oxygen sensors of the types which generate voltages not variable in proportion to the detected concentrations of oxygen. Problems are however met in known oxygen sensors with outputs proportional to oxygen concentrations in that such oxygen sensors are much more susceptible to temperature variation than oxygen sensors with outputs non-proportional to oxygen concentrations. When such a proportional-output oxygen sensor is used in an internal combustion engine which is subject to frequent fluctuations in operating temperature, the voltage output from the sensor will also fluctuate frequently. The voltage output from the oxygen sensor will decrease in response to reduction in the temperature of the exhaust gases from the engine and will increase as the power output of the engine is increased to cause pulsation in the flow of exhaust gases to invite steep fluctuations in the gas pressure in the exhaust system in which the oxygen sensor is located. Such an unstable voltage output from the oxygen sensor will require provision of a sophisticated architecture in the signal processing circuitry to process the signal for the control of the air-to-fuel ratio of the combustible mixture to be supplied to the engine.

It is accordingly a prime object of the present invention to provide an improved electrochemical oxygen sensor assembly adapted to produce an electric output which is less dependent upon temperature fluctuations in the atmosphere to be monitored by the sensor assembly than in a conventional oxygen sensor having a proportional concentration-output characteristic.

It is another important object of the present invention to provide an improved oxygen sensor assembly capable of generating a stable, fluctuation-free electric output in temperature varying environments as in the exhaust system of an internal combustion engine.

It is still another important object of the present invention to provide an improved oxygen sensor assembly which is reliable in performance under temperature varying conditions and which will also provide all the advantages that are achievable by any conventional oxygen sensors having proportional concentration-output characteristics.

It is still another important object of the present invention to provide an improved oxygen sensor assembly in which the diffusion of oxygen molecules into the oxygen sensor assembly is not seriously affected by the possible deposit of contaminant particles at any locations of the assembly.

Yet, it is still another important object of the present invention to provide an improved oxygen sensor assembly which is advantageous for use in the exhaust system of an internal combustion engine which normally involves pulsation in the pressure of the exhaust gases therefrom.

It is still another important object of the present invention to provide an improved oxygen sensor assembly in which, when used in the exhaust system of an internal combustion engine, the oxygen sensing unit forming part of the assembly can be reliably protected from being abruptly cooled down as would otherwise be caused by the direct impingement of exhaust gases involving pulsating gas pressures.

It is still another important object of the present invention to provide an improved oxygen sensor assembly in which, when used in the exhaust system of an internal combustion engine, the pulsating pressure of the exhaust gases admitted into the sensor assembly can be dampened out before the gases reach the oxygen sensing unit forming part of the assembly and enables the sensing unit to detect the concentration of oxygen in the gases flowing into the gap in the sensing unit at practically constant, relatively low pressure levels.

SUMMARY OF THE INVENTION

In accordance with the present invention, there is provided an oxygen sensor comprising (1) an oxygen sensing unit sensitive to oxygen in an oxygen-containing gas and operative to produce an electric signal variable with the concentration of oxygen in the oxygen-containing gas when contacted by a stream of the gas, and (2) a partitioned housing structure which has at least one first port open to the outside of the housing structure and which comprises partition means defining in the housing structure first and second chambers which are located across the partition means, the partition means being formed with at least one second port providing communication between the first and second chambers, the first chamber being open to the first port and the second chamber having enclosed the oxygen sensing unit therein.

BRIEF DESCRIPTION OF THE DRAWINGS

The features and advantages of as oxygen sensor assembly according to the present invention will be more clearly appreciated from the following description taken in conjunction with the accompanying drawings in which:

FIGS. 9 and 10 are views similar to FIGS. 7 and 8, respectively, but show another preferred form of housing structure which may form part of an oxygen sensor assembly according to the present invention, wherein FIG. 9 is taken on planes indicated by lines IX—IX in FIG. 10; and FIGS. 11 and 12 are views also similar to FIGS. 7 and 8, respectively, but show still another preferred form of housing structure which may form part of an oxygen sensor assembly according to the present invention, wherein FIG. 11 is taken on planes indicated by lines XI—XI in FIG. 12.

DESCRIPTION OF THE PREFERRED EMBODIMENTS

Figure 1:
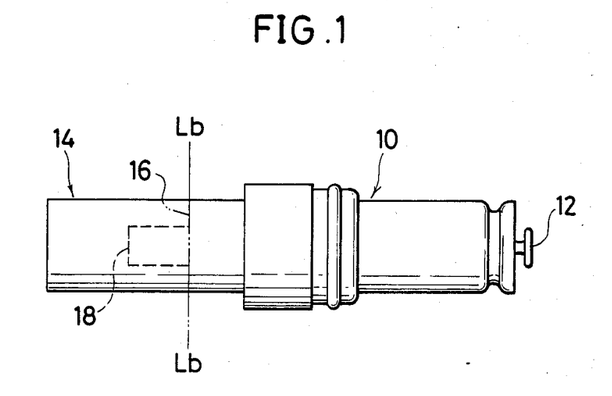
FIG. 1 is a side view showing the external appearance of an oxygen sensor assembly embodying the present invention.

Referring to FIG. 1, an oxygen sensor assembly embodying the present invention is shown comprising a generally cylindrical body structure 10 having at one end thereof a lead plug 12 through which incoming and outgoing lead wires (not shown) are passed into the body structure 10. The body structure 10 has securely coupled thereto a hollow, cylindrical partitioned housing structure 14 which projects axially from the body structure 10 opposite to the lead plug 12 and which thus has a longitudinal direction with respect to the body structure 10. As indicated by dotted lines, the housing structure 14 has housed therein a support member 16 which forms part of the body structure 10 and an oxygen sensing unit 18 is mounted on the support member 16. The support member 16 projects from the interior of the body structure 10 and has an end face within the housing structure 14, with the oxygen sensing unit 18 projecting from the end face of the support member 16 toward a closed end wall of the housing structure 14. Though not shown in the drawings, the oxygen sensor assembly thus constructed generally is assumed to be mounted on the exhaust system of an internal combustion engine with the housing structure 14 inserted at least in part through a suitable wall portion of the exhaust manifold of the engine so that the oxygen sensing unit 18 is at least in part located within a passageway in the exhaust manifold. The oxygen sensing unit 18 is herein assumed as projecting from a base plane indicated by Lb into the passageway in the exhaust manifold from the support member 16. The base plane Lb is perpendicular to the center axis of the housing structure 14 and is shown lying on the end face of the support member 16.

Figure 2:
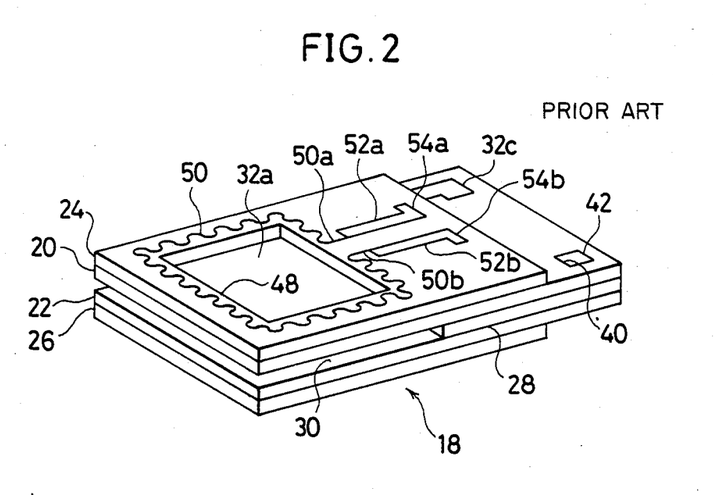
FIG. 2 is a perspective view showing, to an enlarged scale, an oxygen sensing unit which forms part of the sensor assembly illustrated in FIG. 1.

The oxygen sensing unit 18 of the embodiment herein shown is per se known in the art and may be constructed as illustrated in FIG. 2. As shown in FIG. 2, the oxygen sensing unit 18 is provided in the form of a multi-layer structure which largely consists of rectangular, elongated first and second active plates 20 and 22, and first and second electric insulator layers 24 and 26 which are also rectangular in shape. Each of the active plates 20 and 22 has parallel outer and inner major surfaces and each of the insulator layers 24 and 26 has a longitudinal measurement less than that of each active plate as shown and also has parallel outer and inner major surfaces.

The active plates 20 and 22 are coextensive with each other and are coupled together by a spacer layer 28 across which the active plates 20 and 22 are spaced apart in parallel from each other. A gap 30 is thus formed between respective overhung portions of the active plates 20 and 22 where the spacer layer 28 is absent between the plates 20 and 22. As will be readily seen from FIG. 3, the gap 30 formed between the active plates 20 and 22 is defined by four sides adjoining one another and is open to the internal space in the housing structure 14 (FIG. 1) along three of the four sides. The spacer layer 28 is typically patterned so that the layer terminates at one lengthwise end of each active plate and the gap 30 terminates at the opposite lengthwise end of each plate, possibly allowing the gap 30 to account for approximately one-half of the total area of each active plate. Each of the active plates 20 and 22 is constructed of a sintered wafer of an oxygen-ion conductive solid electrolyte and acts as an electrochemical cell. As the oxygen-ion conductive solid electrolyte to form each of such active plates 20 and 22 may be used a solid solution of zirconia (zircinium oxide, $ZrO_2$) mixed with yttria (yttrium oxide, $Y_2O_3$) or calcia (calcium oxide, CaO) as a solute although another type of solid solution such as, for example, cerium dioxide ($CeO_2$), thorium dioxide ($ThO_2$) or hafnium dioxide ($HfO_2$) could also be used alternatively if desired. In the shown construction of the oxygen sensing unit 18, the first active plate 20 is to be used as an pump cell element and the second active plate 22 is to be used as a sensor cell element. The first and second active plates 20 and 22 will thus be hereinafter referred to as pump cell element and sensor cell element, respectively. The spacer layer 28 formed between these pump cell element 20 and sensor cell element 22 may be of any heat-resistive, electrically non-conductive, inorganic adhesive such as a ceramic adhesive.

The insulator layers 24 and 26 are bonded or otherwise securely attached to the cell elements 20 and 22, respectively. Each of these insulator layers 24 and 26 is constructed of an electrically insulating inorganic substance such as alumina or spinel and is to be used as a heater element. The multi-layer structure composed of the cell elements 20 and 22 and spacer layer 28 is in part interposed between the heater elements 24 and 26 and in part project from the heater elements 24 and 26.

Figure 3:
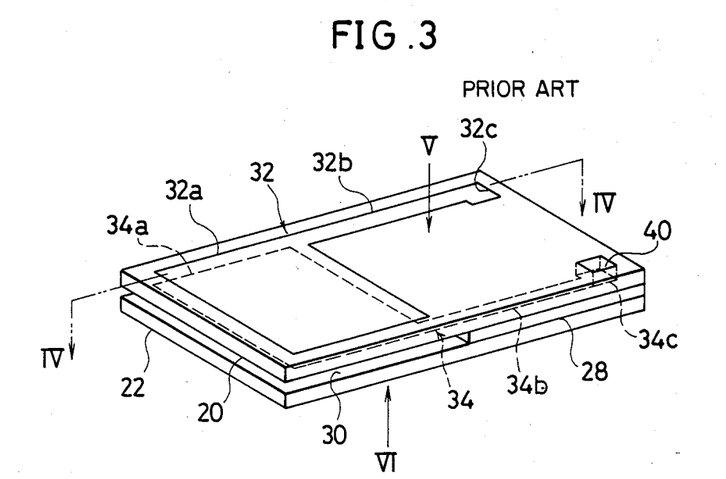
FIG. 3 is a perspective view showing the structure including electrochemically active elements forming part of the oxygen sensing unit illustrated in FIG. 2.
Figure 4:
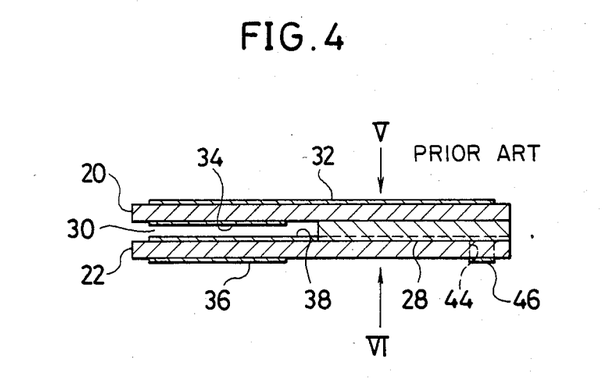
FIG. 4 is a sectional view taken on line IV—IV in FIG. 3.
Figure 5:
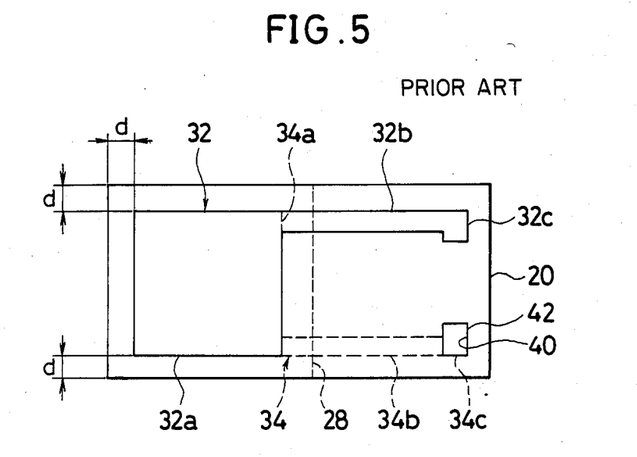
FIG. 5 is a plan view of a pump element which forms part of the structure illustrated in FIG. 1, the pump element being viewed in a direction indicated by arrow V in FIGS. 3 and 4.

As shown in FIGS. 3 and 4, the pump cell element 20 has heat-resistive electrode layers 32 and 34 formed on both of its outer and inner major surfaces, respectively, and likewise the sensor cell element 22 has electrode layers 36 and 38 (not seen in FIG. 3) formed on both of its outer and inner major surfaces, respectively. As will be better seen from FIG. 5, the electrode layer 32 on the outer major surface of the pump cell element 20 has a generally square-shaped major region 32a which has three of its edges respectively extending in parallel with and set back a predetermined distance d inboardly from one lengthwise end edge and the lengthwise extending opposite side edges of the cell element 20. The electrode layer 32 further has an elongated strip region 32b extending along one side edge of the cell element 20 from one of the two corner portions of the major region 32 opposite to the aforesaid lengthwise end edge of the cell element 20. The strip region 32b terminates in a terminal region 32c located immediately ahead of the other lengthwise end edge of the cell element 20. The electrode layer 34 oh the reverse, viz., inner major surface of the pump cell element 20 is patterned in symmetry to the electrode layer 32 with respect to the longitudinal center line of the cell element and has a generally square-shaped major region 34a having three of its edges respectively extending in parallel with and set back the predetermined distance d from one lengthwise end edge and the opposite side edges of the cell element 20. The major region 34a of the electrode layer 34 is thus in registry with the major region 32a of the electrode layer 32 as will be seen from FIG. 3 in which the electrode layer 34 is indicated by dotted lines. The electrode layer 32 on the inner major surface of the cell element 20 further has a strip region 34b extending along the other side edge of the cell element 20 from one of the two corner portions of the major region 34a opposite to the above mentioned lengthwise end edge of the cell element 20. The strip region 34b also terminates in a terminal region 34c located ahead of the other lengthwise end edge of the cell element 20. The corner portions out of which the strip portions 32b and 34b merge are located opposite to each other laterally of the cell element 20 so that the terminal regions 32c and 34c into which the strip portions 32b and 34b respectively merge are also located opposite to each other laterally of the cell element 20. The pump cell element 20 is formed with an aperture 40 located in registry with the terminal region 34c of the electrode layer 34 as shown in FIGS. 3 and 5. The terminal region 34c of the electrode layer 34 is thus conductively connected to a terminal element 42 formed in this aperture 40.

Figure 6:
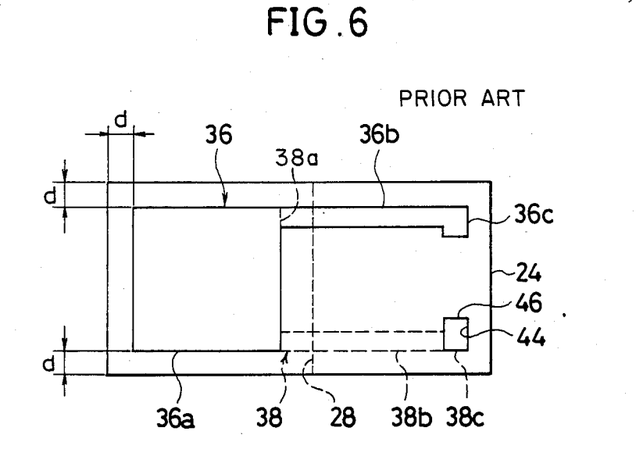
FIG. 6 is a plan view of a sensor element which forms part of the structure shown in FIG. 1, the sensor element being viewed in a direction indicated by arrow VI in FIGS. 3 and 4.

The electrode layers 36 and 38 on the sensor cell element 22 are patterned also similarly to the electrode layers 34 and 32, respectively, on the pump cell element 20. As will be better seen from FIG. 6, the electrode layer 36 on the outer major surface of the sensor cell element 22 has a generally square-shaped major region 36a which has three of its edges respectively extending in parallel with and set back the distance d from one lengthwise end edge and the opposite side edges of the cell element 22. The electrode layer 36 further has a strip region 36b extending along one side edge of the cell element 22 from one of the two corner portions of the major region 36 opposite to the aforesaid lengthwise end edge of the cell element 22. The strip region 36b terminates in a terminal region 36c located ahead of the other lengthwise end edge of the cell element 22. The electrode layer 38 on the inner major surface of the sensor cell element 22 is patterned in symmetry to the electrode layer 36 with respect to the center line of the cell element 22 and has a generally square-shaped major region 38a having three of its edges respectively extending in parallel with and set back the distance d from one lengthwise end edge and the opposite side edges of the cell element 22. The major region 38a of the electrode layer 38 is thus exactly in registry with the major region 36a of the electrode layer 36. The electrode layer 38 on the cell element 22 further has a strip region 38b extending along the other side edge of the cell element 22 from one of the two corner portions of the major region 38a opposite to the aforesaid lengthwise end edge of the cell element 22. The strip region 38b also terminates in a terminal region 38c located ahead of the other lengthwise end edge of the cell element 22. The corner portions out of which the strip portions 36b and 38b respectively merge are located opposite to each other laterally of the cell element 22 so that the terminal regions 36c and 38c into which these strip portions 36b and 38b respectively merge are also located opposite to each other laterally of the cell element 22. The sensor cell element 22 is formed with an aperture 44 located in registry with the region 38c of the electrode layer 38 as shown in FIGS. 4 and 6. The terminal region 38c of the electrode layer 38 is thus connected to a terminal element 46 formed in this aperture 44 as will be seen from FIG. 4. The strip portion 34b of the electrode layer 34 on the pump cell element 20 is in part interposed between the cell element 20 and the spacer layer 28 and, likewise, the strip portion 38b of the electrode layer 38 on the sensor cell element 22 is in part interposed between the cell element 22 and the spacer layer 28.

As will be understood from the above description, the major regions 32a and 34a of the electrode layers 32 and 34 on the pump cell element 20 and the major regions 36a and 38a of the electrode layers 36 and 38 on the sensor cell element 22 are all in registry with each other across the gap 30 between the cell elements 20 and 22. Furthermore, the strip region 32b and terminal region 32c of the electrode layer 32 on the outer major surface of the pump cell element 20 are in registry with the strip region 38b and terminal region 38c, respectively, of the electrode layer 38 on the inner major surface of the sensor cell element 22. Likewise, the strip region 34b and terminal region 34c of the electrode layer 34 on the inner major surface of the pump cell element 20 are respectively in registry with the strip region 36b and terminal region 36c of the electrode layer 36 on the outer major surface of the sensor cell element 22. Each of the electrode layers 32, 34, 36 and 38 is formed preferably of platinum, ruthenium or palladium and may be formed by flame spraying, chemical plating or vacuum deposition techniques using any of these substances.

The first and second heater elements 24 and 26 attached to the cell elements 20 and 22, respectively, are provided with generally square-shaped openings which are represented by the opening 48 formed in the first heater element 24 as shown in FIG. 2. The square-shaped opening 48 in each of the heater elements 24 and 26 has three of its edges respectively extending in parallel with and set back a predetermined distance from one lengthwise end edge and the lengthwise extending opposite side edges of each heater element. The distance which the three edges of the opening 48 are spaced apart from the corresponding edges of each heater element is equal to or slightly larger than the previously mentioned distance d which the three edges of the major region of each of the electrode layers 32, 34, 36 and 38 are spaced apart from the corresponding edges of each cell element. Accordingly, the openings 48 in the heater elements 24 and 26 are at least partly in strict registry with the major regions 32a and 36a of the electrode layers 32 and 36 on the outer major surfaces of the cell elements 20 and 22, respectively. Thus, the major regions 32a and 36a of the electrode layers 32 and 36 are exposed through the openings 48 in the heater elements 24 and 26, respectively, with the heater elements 24 and 26 placed on the outer major surfaces of the cell elements 20 and 20, respectively. On the other hand, the major regions 34a and 38a of the electrode layers 34 and 38 on the inner major surfaces of the cell elements 20 and 22 are exposed to the gap 30 formed between the cell elements 20 and 22. The strip portion 32b of the electrode layer 32 on the pump cell element 20 is in part interposed between the cell element 20 and the first heater element 24 and, likewise, the strip portion 36b of the electrode layer 36 on the sensor cell element 22 is in part interposed between the cell element 22 and the second heater element 26.

The heater elements 24 and 26 have embedded therein or securely received thereon heat generating lines which are represented by the line 50 as shown in FIG. 2. The heat generating line 50 in each of the heater elements 24 and 26 extends preferably in a serpentine zigzag pattern as shown around the square-shaped opening 48 in the heater element and has parallel opposite terminal portions 50a and 50b extending longitudinally of the heater element away from the opening 48 surrounded by the line 50. The heat generating lines 50 are each typically in the form of an electrically and thermally resistive wire of metal such as for example platinum or gold. The terminal portions 50a and 50b of the line 50 terminate in conductive strip layers 52a and 52b, respectively, formed in or on the outer major surface of each of the heater elements 24 and 26 as also shown in FIG. 2. The conductive strip layers 52a and 52b extend longitudinally of each of the heater elements 24 and 26 and in turn terminate in terminal regions 54a and 54b, respectively, which are located adjacent the other end edge of the heater element. These terminal regions 54a and 54b of the conductive strip layers 52a and 52b are also formed of metal such as platinum in or on the outer major surface of each of the heater elements 24 and 26.

Figure 7:
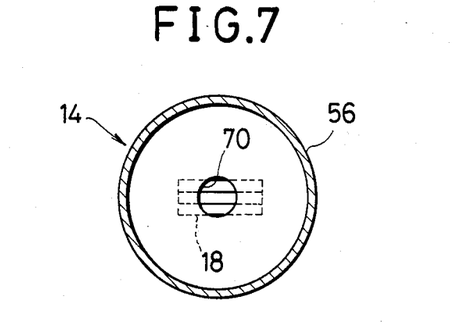
FIG. 7 is a cross sectional view of a preferred form of housing structure which also forms part of the oxygen sensor assembly illustrated in FIG. 1.
Figure 8:
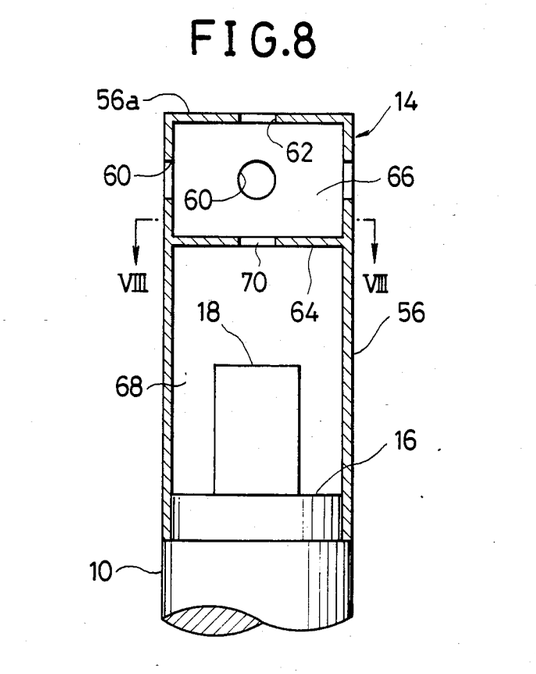
FIG. 8 is a longitudinal sectional view of the housing structure illustrated in FIG. 7 which is taken on base planes indicated by lines VII—VII in FIG. 1.

The oxygen sensing unit 18 constructed as hereinbefore described is housed within the hollow cylindrical partitioned housing structure 14 and is supported by the support member 16 of the body structure 10 as schematically shown by dotted lines in FIG. 1. In the embodiment of an oxygen sensor assembly according to the present invention, the partitioned housing structure 14 comprises a hollow, cylindrical receptacle 56 which is closed at one end by the support member 16 and which has an end wall 56a at its axial end opposite to the support member 16 as shown in FIGS. 7 and 8. The receptacle 56 projects axially from the body structure 10 and is formed with a suitable number of ports 60 in the side wall of its leading end portion and a port 62 located preferably centrally of its end wall 56a. The ports 60 in the side wall portion of the receptacle 56 are shown provided as being four in number and are arranged preferably in symmetry, viz., located at angular intervals of 90 degrees about the center axis of the receptacle 56 as will be seen from FIG. 7. The housing structure 14 further comprises an internal partition 64 spaced apart axially from the end wall 56a of the receptacle 58 to define in the receptacle 56 first and second chambers 66 and 68 which are located in series with each other across the partition. The first chamber 66 is defined axially between the partition 64 and the end wall 56a of the receptacle 56 and is encircled by that side wall portion of the receptacle which is formed with the ports 60. The partition 64 is formed with a port 70 which may be located in alignment with the center port 62 in the end wall 56a of the receptacle 56 as shown, providing communication between the first and second chambers 66 and 68 through the port 70. The second chamber 68 has enclosed therein the oxygen sensing unit 18 which projects from the end face of the support member 16 with the gap 30 in the unit 18 open at its leading end toward the partition 64 as will be seen from FIG. 8. The oxygen sensor assembly being assumed to be used on the exhaust system of an internal combustion engine with the housing structure 14 projecting into the exhaust manifold (not shown), the second chamber 68 in the receptacle 56 is allowed to communicate with a gas passageway in the exhaust manifold through the side and center ports 60 and 62 in the receptacle 56, the first chamber 66 between the end wall 56a and the partition 64 and the center port 70 in the partition 64.

Description will now be made with concurrent reference to FIGS. 1 to 8 regarding the principle of operation of the oxygen sensor assembly thus constructed and arranged. Though not shown in the drawings, the respective terminal regions 54a and 54b of the conductive strip portions 52a and 52b on each of the heater elements 24 and 26 are electrically connected across a suitable source of electric current typically through any current control circuit means. In addition, the respective terminal regions 32c and 34c of the electrode layers 32 and 34 on the pump cell element 20 are electrically connected across a source (not shown) of a d.c. voltage through any voltage control means. A constant d.c. voltage is thus developed across the pump cell element 20 with a positive potential established on the electrode layer 32 on the outer major surface of the cell element 20 and a negative potential established on the electrode layer 34 on the inner major surface of the cell element 20. On the other hand, the respective terminal regions 36c and 38c of the electrode layers 36 and 38 on the sensor cell element 22 are connected to a suitable signal processing circuitry by way of temperature-sensitive current or voltage control means, though not shown in the drawings.

During operation of the sensor assembly, the exhaust gases discharged from the combustion chambers of the engine are partially admitted into the housing structure 14 through the ports 60 and 62, first chamber 66, port 70 and second chamber 68. The exhaust gases thus admitted into the second chamber 68 in the receptacle 56 flow into the gap 30 between the pump cell element 20 and sensor cell element 22 of the oxygen sensing unit 18. By the current (temperature control current) supplied to the heat generating line 50 on each of the heater elements 24 and 26, the heat generating line 50 is activated to generate heat. The heat thus generated is transferred through the heater elements 24 and 26 to the pump cell element 20 and sensor cell element 22, respectively. A d.c. voltage (pump voltage) being developed across the pump cell element 20, oxygen ions are caused to migrate through the oxygen-ion conductive bulk of the pump cell element 20 from the major region 34a of the negative inner electrode layer 34 to the major region 32a of the positive outer electrode layer 32. As a result of such movement of oxygen ions through the pump cell element 20, the oxygen molecules contained in the exhaust gases in the gap 30 between the pump cell element 20 and sensor cell element 22 are diffused into the oxygen depleted pump cell element 20 and are expelled out of the cell element 20. As the oxygen molecules are pumped out of the gap 30, there is produced a gradual decrease in the concentration of oxygen in the gap 30 so that a differential is progressively created between the concentration of oxygen in gases in the gap 30 and the concentration of oxygen in the ambient gases in which the oxygen sensor assembly is immersed within the receptacle 14. Upon lapse of a certain incipient transient period, a steady state is reached at which the number of the oxygen molecules pumped out of the gap 30 is equalized with a flux of oxygen molecules allowed into the gap 30 through the three open edges of the gap 30. Under such a steady state condition, the average pumped oxygen partial pressure $P_a$ in the gap 30 assumes a value smaller than the non-pumped oxygen partial pressure $P_c$ in the exhaust gases surrounding the oxygen sensing unit 18. The differential oxygen partial pressure developed between the fluxes of gases inside and the gases outside acts on the sensor cell element 22, which is therefore caused to induce thereacross an electromotive force E which varies with the pumped and non-pumped oxygen partial pressures $P_a$ and $P_c$. As well known in the art, this electromotive force E is given by the Nernst equation:

$$E = (RT/4F) * ln(P_c/P_a),$$

where R is the ideal gas constant, T is the absolute temperature of the unit 18, and F is the Faraday's constant. Under the steady state conditions, the electromotive force E thus induced across the sensor cell element 22 can be maintained at a desired fixed value if the pump current through the cell element 20 is controlled to vary appropriately. The pump current controlled in this fashion is known to vary approximately in linearly proportional relationship to the concentration of the non-pumped oxygen in the gases surrounding the oxygen sensing unit 18 with the temperature T of the unit 18 maintained at a fixed value. This temperature T of the sensing unit 18 can be maintained constant by controlling the current to be supplied to each of the heat generating lines 50 through the associated conductive strip layers 52a and 52b (FIG. 2). The heat applied to the pump cell element 20 and sensor cell element 22 through the heater elements 24 and 26, respectively, thus provides temperature compensation for the pump current to achieve enhanced accuracy of the oxygen detection. The heat applied to the cell elements 20 and 22 is effective not only to provide such temperature compensation but also to promote the electrochemical activity of each cell element of the oxygen-ion conductive solid electrolyte, particularly the oxygen pumping activity of the pump cell element 20 especially at low temperatures of the exhaust gases to which the oxygen sensing unit 18 is to be exposed. Where the temperature compensation for the pump current is not a serious requirement, the heater elements 24 and 26 might therefore be omitted from the oxygen sensor assembly although this would be detrimental to the electrochemical activities of the cell elements 20 and 22.

The pump current controlled to vary in relation to the electromotive force E and compensated for by the temperature T is used as a signal current in the aforesaid signal processing circuit. The signal current is processed so that the concentration of the exhaust gases being monitored by the oxygen sensor assembly is determined with an excellent degree of accuracy which can be achieved by the linearly varying characteristic of the pump current.

Figure 9:
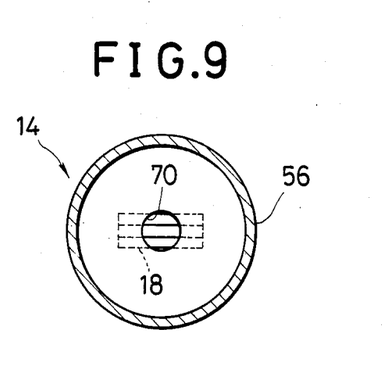
Figure 10:
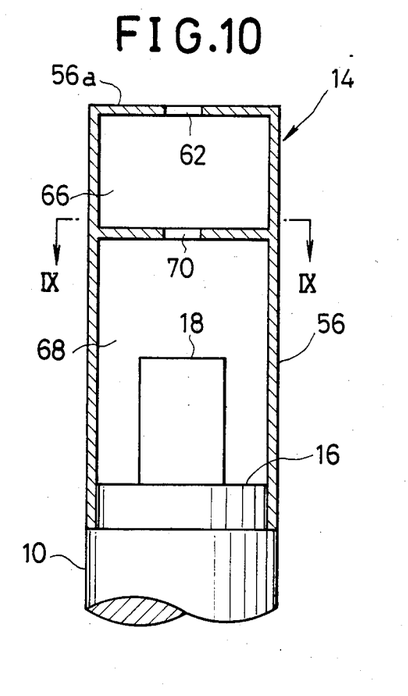

While the receptacle 56 of the oxygen sensor assembly embodying the present invention as hereinbefore described is provided with not only the port 62 in its end wall 56a but also the ports 60 in its side wall, only the port 62 in the end wall 56a of the receptacle 56 may be provided with the side wall of the receptacle left totally blind. FIGS. 9 and 10 show such a construction of the housing structure 14.

Figure 11:
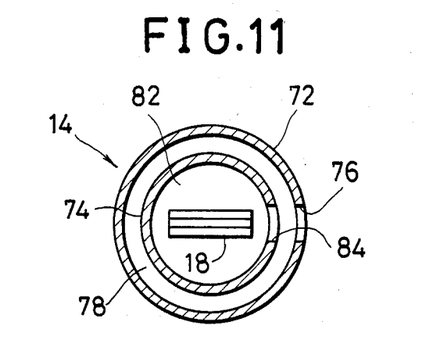
Figure 12:
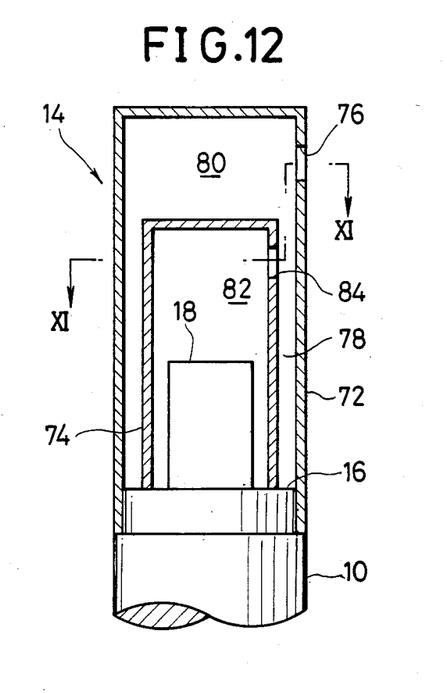

Alternatively, the housing structure of an oxygen sensor assembly according to the present invention may be of the dual-shell construction as shown in FIGS. 11 and 12. The dual-shell housing structure 14 is composed of hollow outer and inner shells 72 and 74 which are concentrically positioned about the center axis of the housing structure 14 and each having a closed end wall at its axial end opposite to the body structure 10 as shown in FIGS. 7 and 8. The outer shell 72 projects axially from the body structure 10 and is formed with a suitable number of ports 76 in its side wall. These ports 76 in the outer shell 72 are preferably located on a plane perpendicular to the center axis of the shell 72 and arranged preferably in symmetry about the center axis of the shell 72. The inner shell 74 has a cylindrical base wall portion concentrically interposed between a base wall portion of the outer shell 72 and the support member 16 of the body structure 10. The inner shell 74 projects axially from the end face of the support member 16 into the outer shell 72 and is radially spaced apart inwardly from the outer shell 74. A generally cylindrical gap portion 78 is thus formed between the side walls of the outer and inner shells 72 and 74 as shown. The end wall of the inner shell 74 is also spaced apart axially from the end wall of the outer shell 74 to form therebetween an end gap portion 80 in which the cylindrical gap portion 78 axially terminates. The gap portions 78 and 80 thus formed between the outer and inner shells 72 and 74 constitute in combination a continuous first chamber 78/80 of the housing structure 14. The inner shell 74 surrounded by such a chamber 78/80 has defined therein a second chamber 82 of the housing structure 14 and has formed in its cylindrical wall portion a suitable number of ports 84 each providing communication between the first chamber 78/80 between the outer and inner shells 72 and 74 and the second chamber 82 in the inner shell 74. The oxygen sensing unit 18 projects from the end face of the support member 16 into the second chamber 82 with the gap 30 (FIGS. 2 to 4) in the unit 18 open at its leading end toward the closed end wall of the inner shell 74 as will be seen from FIG. 12. The ports 84 in the inner shell 74 are located on a plane perpendicular to the center axis of the shell 74 and relatively remote from the open end of the gap 30 in the oxygen sensing unit 18 and are also arranged preferably in symmetry about the center axis of the shell 74 as will be seen from FIG. 11. The oxygen sensing unit 18 per se is also positioned to be symmetrically about the center axis of the inner shell 74 with the gap 30 between the cell elements 20 and 22 open at its lengthwise end toward the end wall of the shell 74. The plane on which the ports 76 in the outer shell 72 are located may be, in the longitudinal direction of the housing structure 14, remoter from the open leading end of the gap 30 in the oxygen sensing unit 18 than the plane on which the ports 84 in the inner shell 72 are located. The oxygen sensor assembly being assumed to be used on the exhaust system of an internal combustion engine with the housing structure 14 projecting into the exhaust manifold (not shown), the second chamber 82 in the inner shell 74 is allowed to communicate with a gas passageway in the exhaust manifold through the ports 76 in the outer shell 72, the first chamber 78/80 between the outer and inner shells 72 and 74 and the ports 84 in the inner shell 74.

An oxygen sensor assembly according to the present invention is characterized, inter alia, by the construction of the housing structure 14 and for this reason may use an oxygen sensing unit of another type provided the alternative sensing unit is capable of providing results of detection comparable to those achievable by the sensing unit of the described type. The oxygen sensing unit 18 used in the embodiment described is however preferred because, in the first place, the diffusion of oxygen molecules into the oxygen sensing unit is not seriously affected by the possible deposit of contaminant particles such as the exhaust-gas borne carbon particles at any locations of the unit. The gap 30 is open along its three sides and permits entry of exhaust gases thereinto through such three-directional openings and, thus, the deposits of such contaminant particles could not successfully interfere with the admission of the gases into the gap 30. This will also provide an assurance of a prolonged lifetime of an oxygen sensor assembly using the oxygen sensing unit 18 of the described nature. Other benefits which can be enjoyed by the use of the oxygen sensing unit 18 include the simplicity of construction and the ease of design modification to provide desired output characteristics.

Nevertheless, the most prominent feature of an oxygen sensor assembly according to the present invention resides in the provision of the housing structure 14 formed with two chambers 66 and 68 defined by the partition 64 (FIGS. 7 to 10) or two chambers 78/80 and 82 defined by the outer and inner shells 56 and 58 (FIGS. 11 and 12). With the provision of such two discrete chambers in the housing structure 14, the pulsating gas pressure of the exhaust gases admitted into the housing structure 14 is dampened out primarily in the first chamber 66 or 78/80 and secondarily when admitted into the second chamber 68 or 82 past the port 70 in the partition 64 or the ports 84 in the outer shell 72. The first chamber 66 or 78/80 thus serves as a surge absorption reservoir to dampen out the pulsating gas pressure being admitted into the second chamber 66 or 82. The exhaust gases with the initially pulsating gas pressure are in this manner permitted to acquire practically constant, relatively low pressure levels before the gases reach the gap 30 in the sensing unit 18 and enable the sensing unit 18 to detect the concentration of oxygen in the gases under stable conditions. The oxygen sensing unit can therefore be protected from being abruptly cooled down as would otherwise be caused by the direct impingement of the blows of exhaust gases involving pulsating gas pressures. Preclusion of such a cooling effect will also lead to and is advantageous for achievement of a signal output with a limited degree of fluctuations.

What is claimed is:

1. An oxygen sensor comprising:
 (1) an oxygen sensing unit being sensitive to oxygen in an oxygen-containing gas and operative to produce an output signal having a magnitude proportional to the concentration of oxygen in the oxygen-containing gas when contacted by a stream of the gas and having a sensor call element made of a first active plate of an oxygen-ion conductive solid electrolyte and a first pair of electrodes sandwiching said active plate, a pump cell element made of a second active plate of an oxygen-ion conductive solid electrolyte and a second pair of electrodes sandwiching said active plate, said first and second active plates confronting a restricted region into which said oxygen-containing gas is introduced and means for applying a pump voltage across said second pair of electrodes to obtain an electric signal having a magnitude related to said pump voltage and/or a sensor voltage appearing across said first pair of electrodes, said voltage being said output signal, and
 (2) a partitioned housing structure which has at least one first port open to theoutside of the structure and which comprises partition means defining in the housing structure first and second chambers which are located across the partition means, the partition means being formed with at least one second port providing communication between the first and second chambers, the first chamber being open to said first port and said second chamber having enclosed said oxygen sensing unit therein, said housing structure including a receptacle formed with said first port, said partition means comprising a partition wall integral with the receptacle and formed with said second port, said first and second chambers being disposed in series with each other across said partition wall, said receptacle further having an end wall axially spaced from said partition wall with said first chamber defined between the end wall and the partition wall, said first port being located in said end wall of the receptacle.

2. An oxygen sensor comprising
an oxygen sensing unit sensitive to oxygen in an oxygen-containing gas and operative to produce an electric signal variable with the concentration of oxygen in the oxygen-containing gas when contacted by a stream of the gas,
a partitioned housing structure which has at least one first port open to the outside of the housing structure and which comprises partition means defining in the housing structure first and second chambers which are located across the partition means, the partition means being formed with at least one second port providing communication between the first and second chambers, the first chamber being open to said first port and said second chamber having enclosed said oxygen sensing unit therein,
said housing structure comprising a receptacle formed with said first port.
said partition means comprising a partition wall integral with the receptacle and formed with said second port,
said first and second chambers being disposed in series with each other across said partition wall, and
said first and second ports being substantially aligned with each other longitudinally of said receptacle.

3. An oxygen sensor comprising
an oxygen sensing unit sensitive to oxygen in an oxygen-containing gas and oeprative to produce an electric signal variable with the concentration of oxygen in the oxygen-containing gas when contacted by a stream of the gas, a partitioned housing structure which has at least one first port open to the outside of the housing structure and which comprises partition means defining in the housing structure first and second chambers which are located across the partition means, the partition means being formed with at least one second port providing communication between the first and second chambers, the first chamber being open to said first port and said second chamber having enclosed said oxygen sensing unit therein, said housing structure comprising a receptacle formed with said first port, said partition means comprising a partition wall integral with the receptacle and formed with said second port, said first and second chambers being disposed in series with each other across said partition wall, said receptacle having an end wall axially spaced apart from said partition wall with said first chamber defined between the end wall and the partition wall and a side wall encircling the first chamber, and said first port being formed in said end wall.

4. An oxygen sensor comprising:
(1) an oxygen sensing unit being sensitive to oxygen in an oxygen-containing gas and oeprative to produce an output signal having a magnitude proportional to the concentration of oxygen in the oxygen-containing gas when contacted by a stream of the gas and having a sensor element made of a first active plate of an oxygen-ion conductive solid electrolyte and a first pair of electrodes sandwiching said active plate, a pump cell element made of a second active plate of an oxygen-ion conductive solid electrolyte and a second pair of electrodes sandwiching said active plate, said first and second active plates confronting a restricted region into which said oxygen-containing gas is introduced and means for applying a pump voltage across said second pair of electrodes to obtain an electric signal having a magnitude related to said pump voltage and/or a sensor voltage appearing across said first pair of electrodes, said voltage being said output signal, and (2) a partitioned housing structure comprising an outer shell and an inner shell enclosed within the outer shell and spaced apart inwardly from the outer shell to form a first chamber therebetween, said outer shell being formed with a first port, said inner shell being formed with a second port, the inner shell having defined therein a second chamber having said oxygen sensing unit fixedly held in position therewithin, from said oxygen sensing unit than the second port in the longitudinal direction of said housing structure, said outer and inner shells having respective generally cylindrical wall portions radially spaced apart from each other to form a generally cylindrical gap portion therebetween and respective end walls axially spaced apart from each other to form therebetween an end gap portion merging into said generally cylindrical gap portion.

* * * * *